US00PP30076P3

(12) United States Plant Patent
Van Swieten

(10) Patent No.: US PP30,076 P3
(45) Date of Patent: Jan. 8, 2019

(54) ***PHALAENOPSIS* ORCHID PLANT NAMED 'PHALFASWI'**

(50) Latin Name: ***Phalaenopsis* hybrid**
Varietal Denomination: PHALFASWI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 17 days.

(21) Appl. No.: 15/731,149

(22) Filed: Apr. 26, 2017

(65) Prior Publication Data

US 2018/0317358 P1 Nov. 1, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ... A01H 5/02; A01H 5/00; A01H 5/08; A01H 6/62
See application file for complete search history.

(56) References Cited

U.S. PATENT DOCUMENTS

PP27,203 P3 * 9/2016 Van Swieten ..... Plt./311
2018/0153077 P1 * 5/2018 Van Swieten ..... Plt./311

OTHER PUBLICATIONS

Upov Pluto Plant Variety Database Jun. 30, 2018, retrieved on Jul. 3, 2018, retrieved from the Internet at https://www3.wipo.int/pluto/user/en/index.jsp, one page. (Year: 2018).*
EU Community Plant Variety Rights Application No. 2016/2205, Application n°A201602175, filed Sep. 13, 2016, 8 pages.
EU Community Plant Variety Office Official Gazette, Jun. 2016, Dec. 15, 2016, cover page and pp. 37, 55.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALFASWI', particularly characterized by having small, dark red-purple, flecked and edged flowers, 1 to 3 peduncles that are medium long and sturdy, leaves that are oblong, 2 to 6 flowering lateral branches, and is propagated by meristem tissue culture, is disclosed.

3 Drawing Sheets

Genus and species: *Phalaenopsis* hybrid.
Variety denomination: 'PHALFASWI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFASWI'.

The new *Phalaenopsis* plant is a product of a planned breeding program conducted by the inventor in Bleiswijk, The Netherlands. The objective of this breeding program was to create a new *Phalaenopsis* plant with numerous branches and many attractive and unique, small, dark red-purple, flecked and edged flowers, suitable for potted plant production.

The new *Phalaenopsis* plant 'PHALFASWI' is a result of cross-pollination made by the inventor in August 2007 in Bleiswijk, The Netherlands of the proprietary female, or seed parent, *Phalaenopsis* hybrid '01-2141' (unpatented) with the proprietary male, or pollen parent, *Phalaenopsis* hybrid '21062-029' (unpatented).

The new *Phalaenopsis* was selected by the inventor as a single plant within the progeny of the stated cross-pollination in a controlled greenhouse in Bleiswijk, The Netherlands in August 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFASWI' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFASWI' as a new and distinct variety of *Phalaenopsis* plant.

1) Small, dark red-purple, flecked and edged flowers;
2) 1 to 3 peduncles;
3) Peduncle is medium long and sturdy;
4) Shape of the leaf is oblong; and
5) Plant has 2 to 6 flowering lateral branches.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in March 2017. Colors in the photographs may differ from the color values cited in the detailed botanical description, which accurately describe the actual colors of the new variety.

DESCRIPTION OF THE NEW VARIETY

Figure 1:
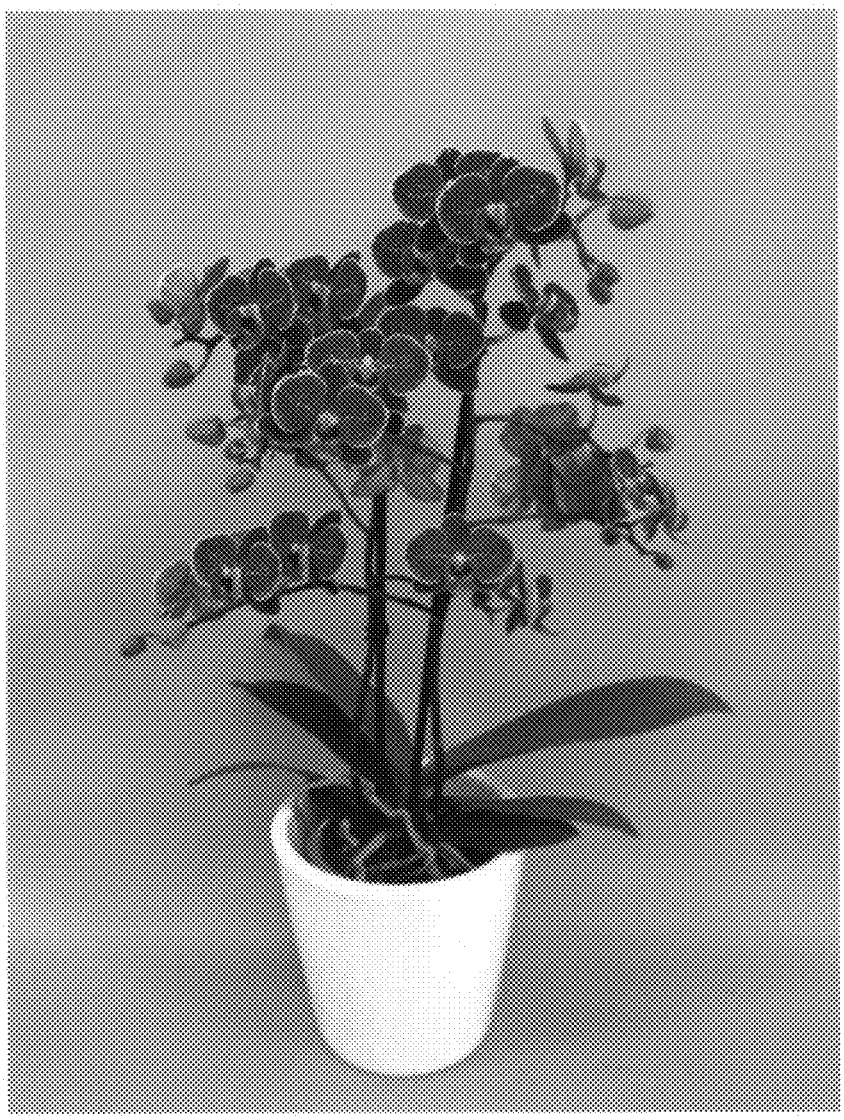
FIG. 1 shows the overall plant habit, including blooms, buds and foliage of 'PHALFASWI'.
Figure 2:
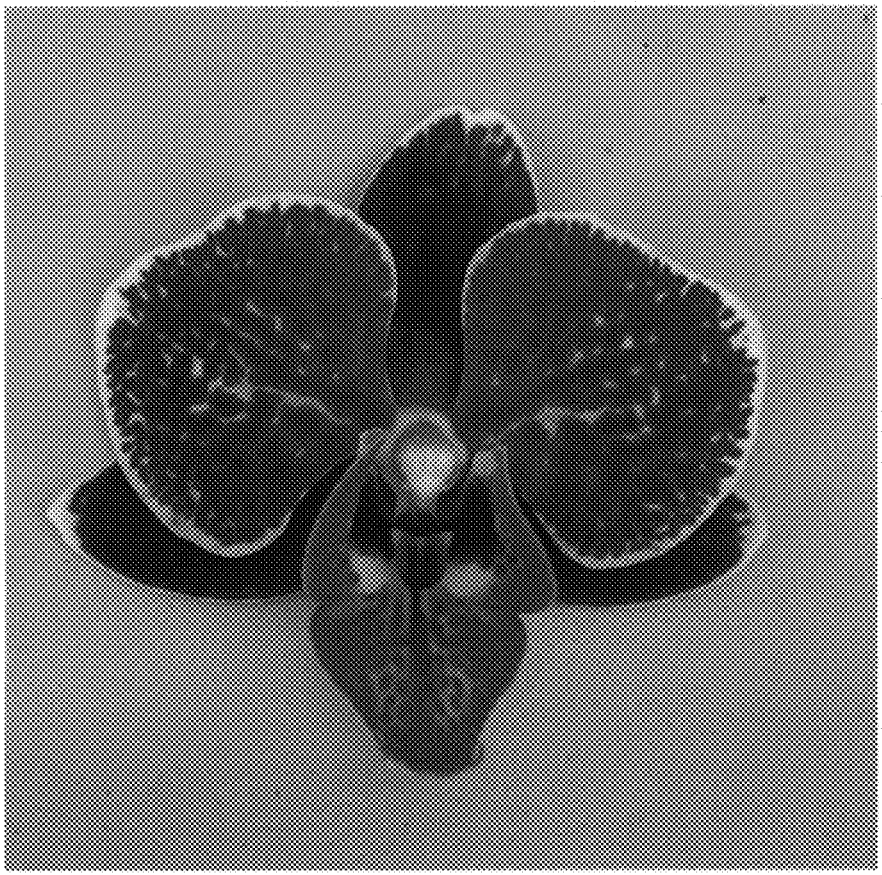
FIG. 2 shows a close-up of a flower of 'PHALFASWI'.
Figure 3:
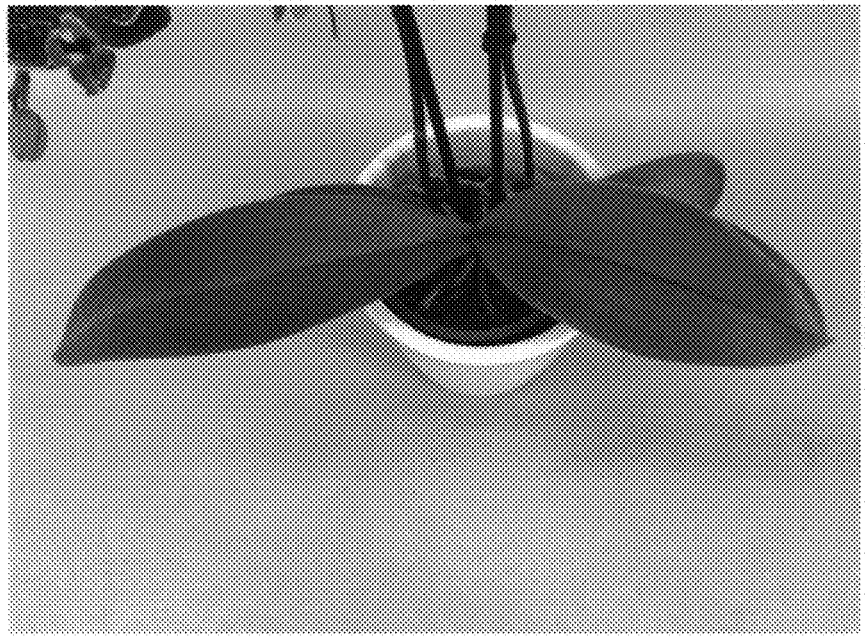
FIG. 3 shows a close-up of the leaves of 'PHALFASWI'.

The following detailed description sets forth the distinctive characteristics of 'PHALFASWI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in March 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFASWI'.

Parentage:

*Female parent*.—*Phalaenopsis* cultivar '01-2141' (unpatented).

*Male parent*.—*Phalaenopsis* cultivar '21062-029' (unpatented).

Propagation:

*Type*.—Meristem tissue culture.

Roots:

*Root description*.—Greyed-green colored roots (between RHS 190B and 190C) with branching lateral roots having light green colored root tips (RHS 144C).

Plant:

*Commercial crop time to flowering*.—Approximately 48 to 50 weeks from a rooted cutting to finish in a 12 cm pot.

*Growth habit of peduncle*.—Standard, green leaves, panicle.

*Height (from soil level to top of inflorescence)*.—Approximately 39.0 cm to 44.0 cm.

*Width (measured from leaf tips)*.—About 33.0 cm to 35.0 cm.

*Vigor*.—Strong.

Leaves:

*Mature leaves*.—Quantity per plant: 7 to 9 leaves are produced before flowering. Length (fully expanded): 17.0 cm to 20.0 cm. Width: 6.5 cm to 7.5 cm. Shape: Oblong. Base shape: Moderately elongated. Apex: Acute unequal. Leaf blade angle with the petiole (measured from the horizontal position): Between 15 degrees and 30 degrees. Leaf margin: Entire. Color: Upper surface: RHS 146A. Lower surface: RHS 146B. Texture: Rough. Thickness: 2.6 mm to 2.8 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—21 to 28.

*Length*.—39.0 cm to 44.0 cm.

*Diameter*.—4.7 mm to 5.0 mm.

*Strength*.—Strong.

*Aspect*.—Upright to slightly pendant.

*Texture*.—Slightly rough.

*Color*.—Mix of green (RHS 146B) and brown (RHS N200A).

*Internode length*.—50.0 mm to 60.0 mm.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 210.0 mm to 250.0 mm.

*Flowering time*.—First flowers can be expected 10 to 11 months after planting in a 12 cm (diameter) pot.

*Flower*.—Height: 45.0 mm to 47.0 mm. Diameter: 53.0 mm to 55.0 mm. Depth of lip: 16.0 mm to 18.0 mm.

*Flower longevity*.—On the plant: 10 to 13 weeks.

*Fragrance*.—Absent.

*Flower bud*.—Average size: Medium. Length: 15.0 mm to 17.0 mm. Width: 12.0 mm to 14.0 mm. Shape: Egg shaped. Color: Red-purple (RHS N77D) and green (RHS 195B).

*Petals*.—Arrangement: Open/free. Shape: Semi-circular. Apex: Obtuse. Margin: Slightly undulated. Length (from base to tip): 22.0 mm to 24.0 mm. Width: 27.0 mm to 29.0 mm. Color (when fully opened): Upper surface: Basic color: Dark red-purple (RHS N79C) with many small flecks (RHS N75C). Over color: Light purple (RHS N75C); white edge (RHS NN155C). Lower surface: Basic color: Light purple (RHS 76B). Over color: Diluting red-purple (RHS N79D); white edge (RHS NN155C).

*Dorsal sepal*.—Shape: Elliptic. Apex: Rounded symmetric. Margin: Entire. Length (from base to tip): 27.0 mm to 29.0 mm. Width: 17.0 mm to 19.0 mm. Color (when fully opened): Upper surface: Basic color: Dark red (RHS 187B) with a moderate number of small flecks (RHS N79C). Over color: Dark red-purple (RHS N79C); white edge (RHS NN155C). Lower surface: Basic color: Light purple (RHS N75D). Over color: Diluting dark red-purple at the base (RHS N79B) and white edge (RHS NN155C).

*Lateral sepals*.—Shape: Ovate. Apex: Obtuse asymmetric. Margin: Entire. Length (from base to tip): 37.0 mm to 39.0 mm. Width: 15.0 mm to 17.0 mm. Color (when fully opened): Upper surface: Basic color: Dark red (between RHS 187B and 187C) with a moderate number of small flecks (RHS N75C). Over color: Dark red-purple (RHS N79C); white edge (RHS NN155C). Lower surface: Basic color: Light purple (RHS N75D). Over color: Red-purple at the base (RHS N79B) and white edge (RHS NN155C).

*Labellum* (*lip*).—Whiskers: Present. Length of whiskers: 2.0 mm to 4.0 mm. Color of whiskers: Purple (RHS N78A and N78B). Pubescence on the lip: Absent.

*Lateral lobe*.—Shape: Spatulate. Margin: Entire. Length: 14.0 mm to 16.0 mm. Width: 10.0 mm to 12.0 mm. Color (upper surface): Dark red (RHS 187A) and yellow at the base (RHS 8A); purple (RHS N78A) and dark red (RHS 183B) with a moderate number of red-purple spots (RHS N79B) toward the edge.

*Apical lobe*.—Shape: Ovate. Margin: Entire. Length: 17.0 mm to 19.0 mm. Width: 15.0 mm to 17.0 mm. Color (upper surface): Yellow (RHS 8A) and dark red at the base (RHS 59A/B); light purple (RHS N75D) and purple (RHS N78A) toward the whiskers, with a moderate number of purple-red spots (RHS 71A).

*Callus*.—Average size: Small. Height: 0.4 cm to 0.5 cm. Length: 0.3 cm to 0.4 cm. Width: 0.3 cm to 0.4 cm. Color: Dark red in the middle (RHS 187A); light yellow on the sides (RHS 8A and 8C).

Reproductive organs:

*Column*.—Length: 8.0 mm to 10.0 mm. Diameter: 4.1 mm to 4.3 mm. Color: Purple (RHS N78B).

*Pollinia*.—Quantity: 2. Diameter: 0.8 mm to 1.0 mm. Color: Orange (RHS 26A).

*Ovary*.—Length: 6.0 mm to 8.0 mm. Diameter: 1.8 mm to 2.0 mm.

*Pedicel*.—Length: 23.0 mm to 25.0 mm. Diameter: 2.0 mm to 2.2 mm. Color: Green at the base (RHS 146A) and light purple (RHS N75A and N75D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND SIMILAR COMMERCIAL VARIETIES

The female parent plant of 'PHALFASWI', cultivar '01-2141' (unpatented), is no longer in existence, so a meaningful comparison cannot be made.

'PHALFASWI' differs from male parent plant '21062-029' (unpatented) in that 'PHALFASWI' has purple whiskers and dark red-purple flowers with ovate apical lobes, whereas '21062-029' has light yellow whiskers and white flowers with triangular apical lobes. Additionally, 'PHALFASWI' has smaller flowers than '21062-029'.

'PHALFASWI' is most similar to the commercial *Phalaenopsis* plants named 'PHALFEQBIN' (U.S. Plant Pat. No. 29,615) and 'PHALDISAM' (U.S. Plant Pat. No. 27,203). 'PHALFASWI' differs from the commercial variety 'PHALFEQBIN' in that 'PHALFASWI' has dark red-purple flowers with ovate apical lobes and peduncles that are a mix of green and brown (RHS N200A), whereas 'PHALFEQBIN' has white flowers with light and dark purple spots, triangular apical lobes and brown (RHS 200B) peduncles with a touch of green. Additionally, 'PHALFASWI' has smaller flowers and much shorter whiskers than 'PHALFEQBIN'.

'PHALFASWI' differs from the commercial variety 'PHALDISAM' in that 'PHALFASWI' has dark red-purple flowers with ovate apical lobes and peduncles that are a mix of green and brown (RHS N200A), whereas 'PHALDISAM' has white flowers with red-purple/greyed-purple flecks, trullate apical lobes and brown (RHS 200C) peduncles. Additionally, 'PHALFASWI' has much smaller flowers and much shorter whiskers than 'PHALDISAM'.

I claim:

1. A new and distinct variety of *Phalaenopsis* plant named 'PHALFASWI', substantially as described and illustrated herein.

* * * * *